(12) United States Patent  
Taylor

(10) Patent No.: US 7,445,637 B2
(45) Date of Patent: Nov. 4, 2008

(54) VERTEBRA STABILIZING ASSEMBLY

(76) Inventor: Jean Taylor, 141 rue d'Antibes, Eden Palace, Cannes (FR) F-08400

( * ) Notice: Subject to any disclaimer, the term of this patent is extended or adjusted under 35 U.S.C. 154(b) by 858 days.

(21) Appl. No.: 10/486,046

(22) PCT Filed: Aug. 8, 2002

(86) PCT No.: PCT/FR02/02834

§ 371 (c)(1),
(2), (4) Date: Jul. 2, 2004

(87) PCT Pub. No.: WO03/015646

PCT Pub. Date: Feb. 27, 2003

(65) Prior Publication Data

US 2004/0243239 A1 Dec. 2, 2004

(30) Foreign Application Priority Data

Aug. 8, 2001 (FR) .................. 01 10604

(51) Int. Cl.
*A61F 2/44* (2006.01)
*A61B 17/70* (2006.01)
*A61B 17/58* (2006.01)

(52) U.S. Cl. .................. 623/17.16; 606/249; 606/99
(58) Field of Classification Search .................. 606/61, 606/248–249; 623/17.11–17.16
See application file for complete search history.

(56) References Cited

U.S. PATENT DOCUMENTS

| | | | |
|---|---|---|---|
| 3,867,728 A * | 2/1975 | Stubstad et al. .......... 623/17.16 |
| 4,904,261 A * | 2/1990 | Dove et al. .............. 623/17.16 |
| 5,496,318 A * | 3/1996 | Howland et al. .............. 606/61 |
| 5,716,416 A | 2/1998 | Lin |
| 6,626,944 B1 * | 9/2003 | Taylor .................... 623/17.16 |
| 6,805,697 B1 | 10/2004 | Helm et al. |
| 2004/0092933 A1 | 5/2004 | Shaolian et al. |
| 2004/0092993 A1 | 5/2004 | Teitebaum et al. |
| 2004/0106940 A1 | 6/2004 | Shaolian et al. |
| 2005/0038514 A1 | 2/2005 | Helm et al. |

FOREIGN PATENT DOCUMENTS

| | | |
|---|---|---|
| DE | 39 22 203 C | 10/1990 |
| EP | 0 743 045 A2 | 11/1996 |
| FR | 2 775 183 A1 | 8/1999 |
| JP | 05 208029 | 8/1993 |
| WO | WO 9942051 A1 * | 8/1999 |
| WO | WO 00/53126 | 9/2000 |
| WO | WO 0053126 A1 * | 9/2000 |

\* cited by examiner

*Primary Examiner*—David J Isabella
*Assistant Examiner*—Julianna N Harvey

(57) ABSTRACT

The invention concerns an assembly comprising: a rear damping implant (10), configured to be laterally placed at the blade-spinal junction of two vertebrae (2, 3) treated without resection of the supra-spinal rear ligament (5), said implant (10) having a height such that, when set in place, it enables, to reset the supra-spinal rear ligament in anatomical tension; and at least a damping interbody implant (11), configured to be inserted between the vertebral end-plates of the two treated vertebrae (2, 3), by the same path used during dissectomy, said implant (11) having a height such that, when set in place, it enables to restore the anatomical height of the intervertebral disc (4) and to reset the front common ligament in anatomical tension.

20 Claims, 3 Drawing Sheets

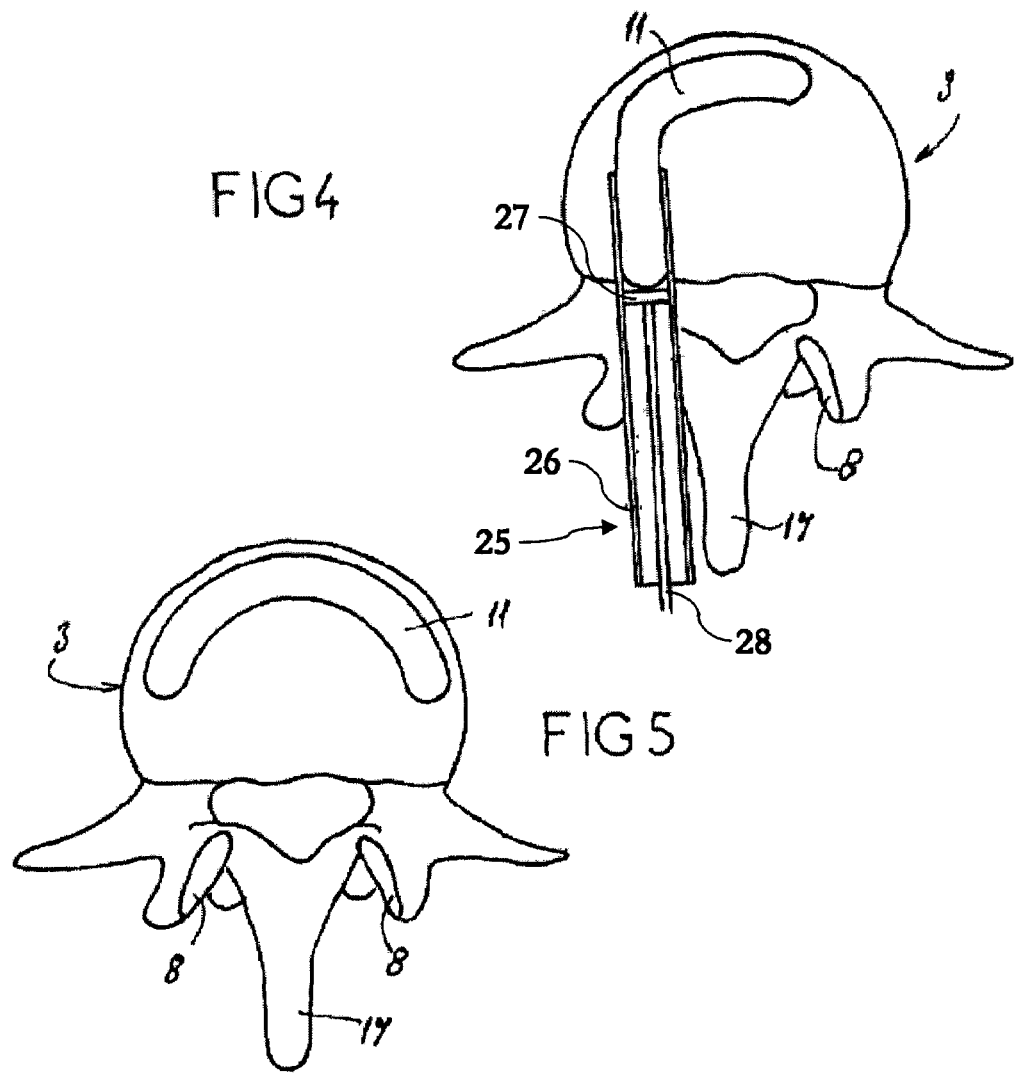
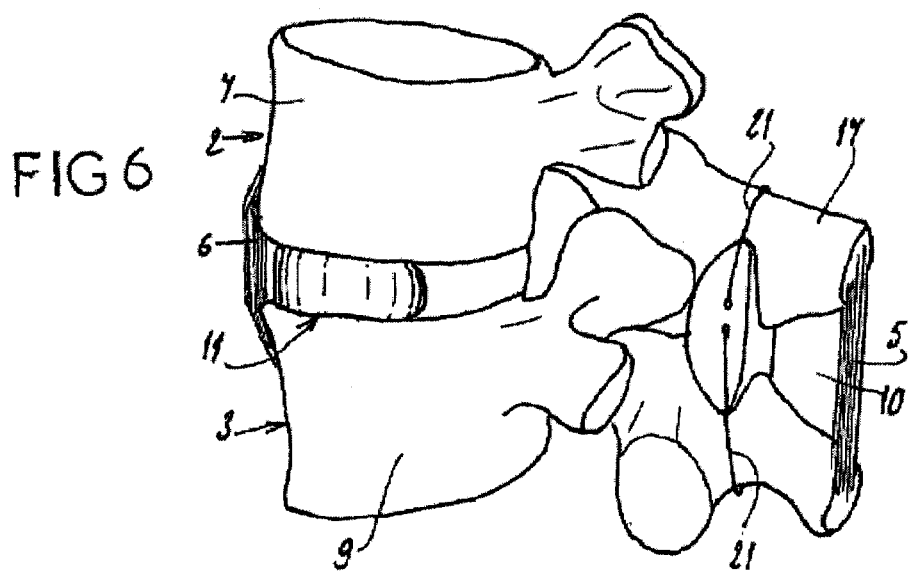

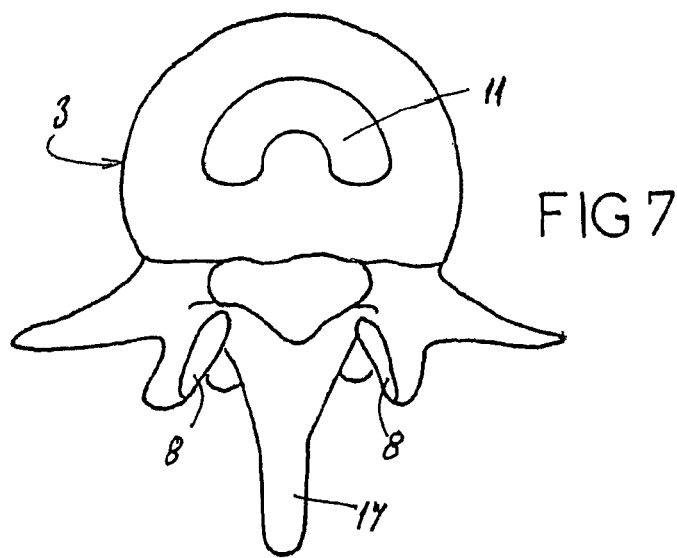
FIG 7
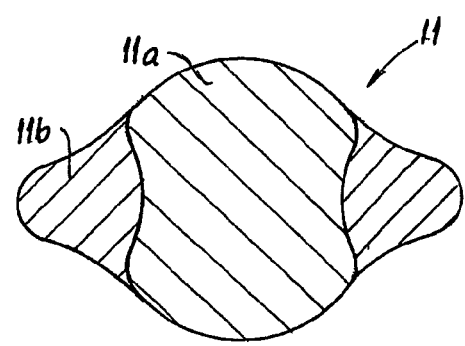
FIG 8
FIG 9
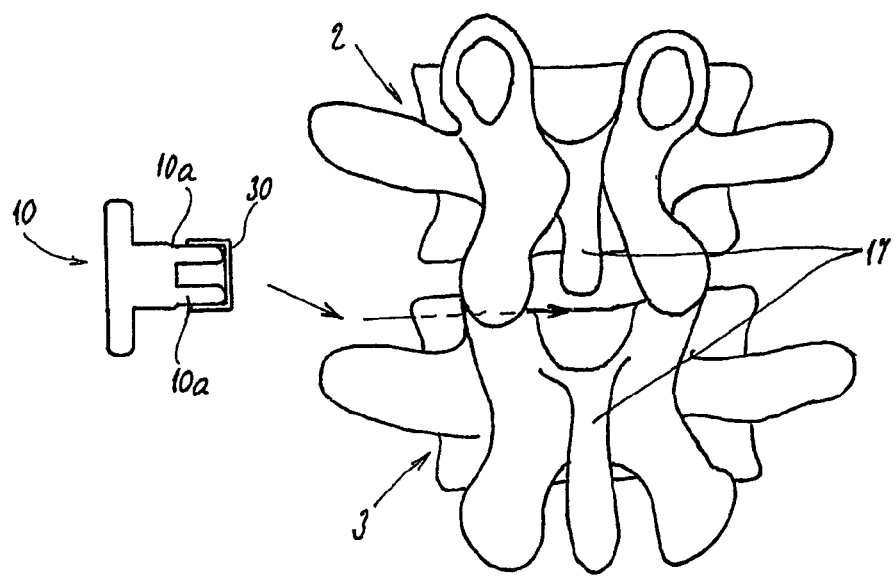

VERTEBRA STABILIZING ASSEMBLY

BACKGROUND

The present invention relates to an assembly for stabilizing vertebrae, in particular lumbar vertebrae. This assembly can be defined as a relief prosthesis having a dual effect, as will be appreciated below.

It is known that the mobility of two adjacent vertebrae, in particular in the lumbar region, is dependent on the intervertebral disc at the anterior side and pairs of articular surfaces at the posterior side.

The arrangement of the disc and articular surfaces ensures auto-limitation of movements both in the plane perpendicular to the vertebral column, during torsion, and in a sagittal plane, during flexions and extensions of the vertebral column.

The shape, the structure and the height of the disc confer on it additional functions of maintaining lordosis, absorbing shocks and distributing stresses. At the rear, the articular surfaces guide the movements and act as hinges.

The ageing process of the subject leads to disturbances in this anterior/posterior equilibrium involving the discs and the surfaces. Generally, the degeneration of the discs precedes that of the surfaces. Collapse and instability of the discs leads to a partial transfer of the stresses to the posterior columns which are formed by the surfaces, which brings about a loss in the surface congruence and a slackening of the ligaments. This results in deterioration of the articular surfaces, which leads to various pathologies having implications of a mechanical and neurological nature.

In order to treat these pathologies, an anterior arthrodesis has been proposed, by insertion of a graft between the plates of the two vertebrae in question. This graft is usually contained in a rigid cage, known as a "fusion cage".

However, this technique does not prevent rotational instability which can compromise, in the medium term, the anticipated antalgic result, and it has now been established that the anterior arthrodesis must be complemented by a posterior arthrodesis.

An intervention of this type has limits and disadvantages. It is aimed at severe pathologies which are at an advanced stage and is not without risks, given that the patients are often treated at a relatively late stage in the pathological development. Intervention can further have consequences which are detrimental to adjacent articulations in the medium-term and long-term.

For these reasons, techniques known as "non-fusion" techniques have been developed and relate to the early and palliative treatment of degenerative disc/surface phenomena.

With regard to the disc space, there have been developed various shock-absorbent implants, which are intended to replace the nucleus pulposus, in the form of pairs of pads or elliptical or spiral elements.

These implants are introduced either via an anterior access point, which has the disadvantage of damaging the anterior common vertebral ligament, or via a posterior access point, which has the disadvantage of leading to the sacrifice of a large amount of bone, owing to the space requirement of the implants.

Techniques involving percutaneous injection of a colloid which can be polymerized in situ have also been proposed, as have techniques using solid, disc-like prostheses in the form of two metal plates which enclose a shock-absorbent material and which rest on each of the vertebral plates which are adjacent to the disc.

These techniques are not completely satisfactory as regards the treatment of disc degeneration combined with wear of the surfaces and/or ligament distension.

Devices intended to limit the articular play of the surfaces have also been proposed. A device of this type comprises in particular a continuous woven ligament which is positioned between the spinous processes or along the articular surfaces by means of pedicle screws, and/or a shock-absorbent dividing element which is positioned at the lamina/spinous process junction so as to alleviate the surface play while at the same time stretching the posterior capsule/ligament elements.

It has been found that these techniques are also not completely satisfactory with regard to the above-mentioned treatment.

SUMMARY

The object of the present invention is to overcome this fundamental disadvantage by providing an assembly for stabilizing two adjacent vertebrae which sustain both disc degeneration with ligament distension, as well as possibly wear of the surfaces, this assembly further having to be relatively simple to implant and, in addition, relatively non-invasive.

According to the invention, this assembly comprises:
- a shock-absorbent posterior implant which is formed to be positioned, via the lateral route, at the lamina/spinous process junction of the two adjacent vertebrae being treated, without resection of the supra-spinous posterior ligament, this posterior implant having a height such that, when it is positioned, it allows the supra-spinous posterior ligament to be reset at anatomical tension; and
- at least one shock-absorbent inter-corporeal implant which is formed to be inserted between the adjacent vertebral plates of the two vertebrae being treated via the same posterior/lateral route as that used during a dissectomy, this implant having a height such that, when it is positioned, it allows the anatomical height of the intervertebral disc to be restored and the anterior common ligament to be reset at anatomical tension.

In this manner, the assembly according to the invention not only allows the anatomical spacing of the vertebrae, both between the surfaces and between the vertebral plates, to be re-established but also allows, and above all with the anterior common ligament and the supra-spinous posterior ligament being conserved, these ligaments to be reset at anatomical tension.

The effect of this tensioning is to restore the anatomical ligament "balance" which exists between these ligaments, while at the same time giving back to the disc and the surfaces the anatomical functions thereof, that is to say, the function of absorbing shocks with regard to the disc and the functions of acting as hinges and of posterior balancing with regard to the surfaces.

The posterior implant is positioned directly behind the surfaces at the site of the inter-spinous ligament complex, and can be stressed in terms of both compression and extension.

The inter-corporeal implant is itself positioned, preferably as far forwards as possible, along the circumference of the vertebral plates. In this manner, it is positioned where the stresses are at a maximum. The maximum spacing thereof from the posterior implant allows the anterior/posterior ligament balance to be optimally re-established.

Therefore, the posterior implant and the inter-corporeal implant have the function of absorbing the stresses, in terms of both compression and extension, which are generated during flexion movements of the vertebral column forwards and backwards. When the vertebral column flexes forwards, the supra-spinous posterior ligament, which is reset at functional tension by the posterior implant, ensures the anatomical function thereof of limiting the movement, which function is optimized and reinforced owing to the relief and the control brought about by the posterior implant, owing to the progressive extension which limits it. At the same time, the inter-corporeal implant provides relief to the defective disc by absorbing the stresses applied in terms of pressure by the superior vertebral body to the lower vertebral body and attenuates the so-called "creep" phenomenon, that is to say, the depression of the disc under the application of pressure. This inter-corporeal implant jointly provides limiting relief which limits the effect of extension which is undergone by the posterior flexible structures. When the vertebral column flexes backwards, the anterior vertebral ligament, which is reset at functional tension by the inter-corporeal implant, ensures the anatomical function thereof of progressively limiting the movement, which function is assisted and reinforced by the extended shock-absorbent implant. At the same time, the posterior implant is compressed and optimizes the play of the surfaces in terms of the function thereof as hinges and of posterior balancing.

The action of each implant is consequently combined with the action of the other implant. Extension of one of the implants is met with compression of the other implant, owing to an interdependent auto-limiting effect.

The use of a single access route further allows the intervention to be greatly simplified and the assembly according to the invention to be made extremely non-invasive.

Securing means are advantageously provided in order to ensure the continuity of the posterior implant in position, relative to the spinous processes. These securing means can comprise a suitable form of the posterior implant, defining opposed recesses for receiving the spinous processes and conferring on the posterior implant a "diabolo" or "H"-like shape, and/or means for fixing the posterior implant to the spinous processes, such as two independent cords or rigid anchoring pieces, which do not limit the deformability of the implant.

The posterior implant can be constituted as a single piece or can be in two parts which can be assembled and which are each brought via one side of the inter-spinous space and are assembled together in this space. When the posterior implant is of a "diabolo" or "H"-like shape and when it is in a single piece, the assembly can comprise a piece which keeps this implant in a deformed state, in which two lateral lugs, which the implant comprises, are brought closer towards each other, in order to allow lateral insertion of the implant between the spinous processes of the vertebrae being treated.

The assembly according to the invention can comprise an inter-corporeal implant which is formed so as to extend in the anterior lateral zones of the vertebral plates in order to reinforce the lateral stability of the vertebrae and to allow relief of the peripheral annulus fibrosis; it can then have, in particular, a curved shape, in the form of a portion of a ring.

The assembly according to the invention can also comprise, instead of or in addition to an inter-corporeal implant for assisting the peripheral annulus fibrosis, an inter-corporeal implant which is provided to replace and/or assist the nucleus. This implant can then be of a general "bean" or "omega"-like shape, with a central portion which is extended by two lateral lobes protruding at the posterior side. It can also be in the form of a sphere.

At least one inter-corporeal implant preferably has a triangular or trapezoidal cross-section and is intended to be implanted with the largest lateral side thereof directed towards the anterior side.

This implant, formed in this manner, corresponds to the anatomical inclination of the disc.

At least one inter-corporeal implant can comprise means for ensuring the securing thereof between the vertebral plates. In particular, these means comprise a form of the inter-corporeal implant, which form is adapted to the shape of the vertebral plates and which can secure this inter-corporeal implant between these plates. When the inter-corporeal implant is in the form of a sphere, it can comprise an equatorial lip which reduces the risk of displacement thereof.

The posterior implant can comprise a core of shock-absorbent material, such as a silicone, a polyurethane, a hydrophilic polymer, a polycarbonate, or a piece of shape-memory metal, and a casing which surrounds the core. This casing allows the core or the piece to be advantageously protected from friction. The casing can be formed from woven fibers.

The inter-corporeal implant can have an identical structure.

The positioning of this inter-corporeal implant can be carried out, in particular, by means of an introduction guide tube which is provided with a piston, the implant being engaged, with compression, in the introduction tube and being able to be expelled therefrom by means of the piston.

The introduction tube temporarily compresses the implant. This reduction in volume, that is to say, in the space requirement of the implant, makes only surgical access similar to that of a dissectomy necessary, avoiding any destabilizing sacrifice of bone. The tube is introduced into the disc space via the transligamentary posterior/lateral route (LVCP). A semi-rigid guide directs and controls the correct positioning of the inter-corporeal implant before being withdrawn by being passed back through the introduction guide tube.

For a correct understanding, the invention is once more described below with reference to the appended schematic drawings which represent, by way of non-limiting examples, a number of possible embodiments of the assembly in question.

BRIEF DESCRIPTION OF THE DRAWINGS

FIGS. 4 and 5 are top views of this inter-corporeal implant, during the introduction thereof between the vertebral bodies, by means of an instrument provided to this end, and after being positioned between these vertebral bodies, respectively;

FIG. 6 is a side view of the two vertebrae after the two implants have been positioned;

FIG. 7 is a view similar to FIG. 5 of an inter-corporeal implant according to another embodiment;

FIG. 8 is a sectioned view of an inter-corporeal implant according to yet another embodiment, and FIG. 9 is a view of a posterior implant, which this assembly comprises, according to another embodiment, and of two vertebrae, on which this implant is to be positioned.

DETAILED DESCRIPTION

Figure 1:
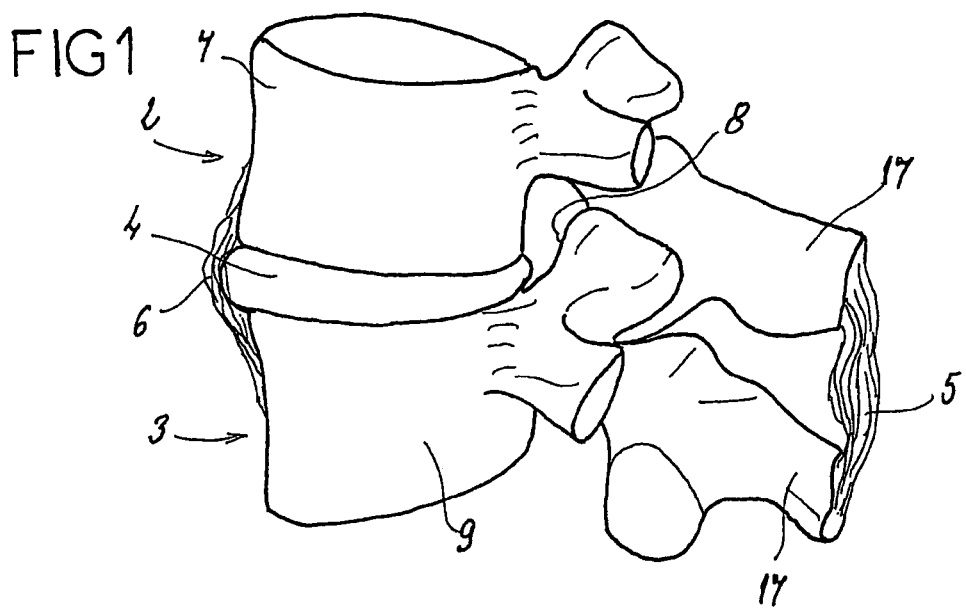
FIG. 1 is a side view of two pathological vertebrae which are to be treated by this assembly.

FIG. 1 shows two vertebrae 2, 3, the intervertebral disc 4 of which has collapsed. This collapse leads to a distension of the supra-spinous posterior ligament 5 and the anterior common ligament 6, excessive stresses on the surfaces 8 in terms of pressure, which can produce lesions thereto, and a risk of contact of the vertebral bodies 7, 9 against each other at the anterior side.

Figure 2:
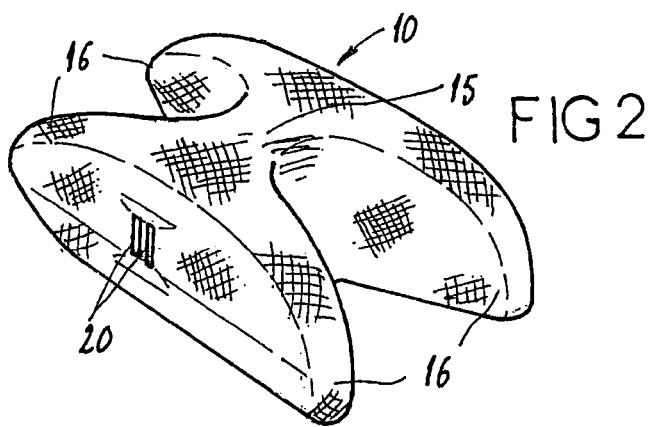
FIG. 2 is a perspective view of a posterior implant, which this assembly comprises, according to one embodiment.
Figure 3:
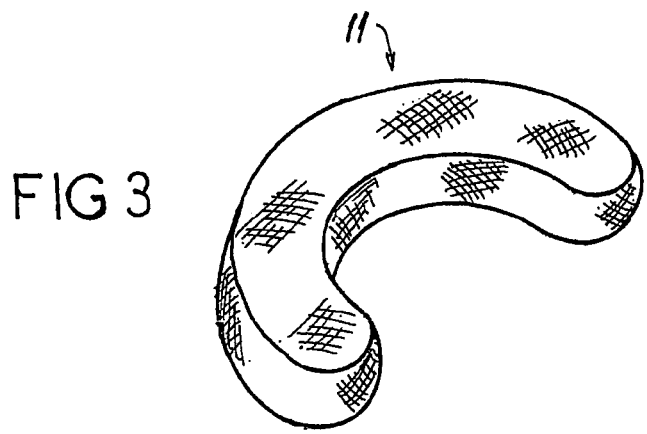
FIG. 3 is a perspective view of an inter-corporeal implant, which this assembly can comprise, according to one embodiment.

In order to treat this pathology, the invention proposes an assembly of two implants 10, 11, acting jointly, that is to say, a posterior implant 10, which can be seen in FIG. 2, and an inter-corporeal implant 11, which can be seen in FIG. 3.

The posterior implant 10 is formed by a core of silicone which is surrounded by a woven casing, in particular of polyester fibers, which ensures the protection of this core. It has an inter-spinous portion 15 and two pairs of lateral lugs 16 which protrude longitudinally at one side and the other of this portion 15.

The portion 15 has a thickness slightly greater than the anatomical inter-spinous space when the vertebrae 2, 3 are in lordosis, so that the portion 15 is slightly compressed by the spinous processes 17 when the implant 10 is positioned at the lamina/spinous process junction. The implant 10 thereby allows, in this position, the supra-spinous posterior ligament 5 to be reset at anatomical tension.

The portion 15 is perforated by two transverse channels 20 which are intended to receive, as shown in FIG. 6, two independent cords 21. These cords 21 serve to connect the implant 10 securely to the processes 17. Each cord 21 can be constituted by a braid, one end of which is crimped to the end of a curved insertion needle and the other end of which comprises a ring which is to be crimped to the cord 21 after the cord has been secured tightly to the corresponding process 17.

The lugs 16 have substantial heights relative to the total height of the implant 10 in the order of, for the upper and lower lugs, 33% and 40% of the total height, respectively. The internal faces of two lugs 16 of the same pair of lugs are inclined so as to converge towards each other in the direction towards the base of the recess which they together delimit. The lugs 16 further have a relatively large mean thickness relative to the mean width of the implant 10 in the order of, for the upper and lower lugs, 27% and 30% of this mean width, respectively.

These lugs 16 allow the securing of the implant 10 between the processes 17 to be ensured in spite of the relative movements of the vertebrae 2, 3, in particular the pivoting movements about the axis of the vertebral column.

The inter-corporeal implant 11 is also formed by a core of silicone which is surrounded by a woven casing, in particular of polyester fibers, ensuring the protection of this core. It has a curved shape, in the form of a portion of a ring, and is sized so as to extend, after positioning, along a wide anterior portion of the peripheral edges of the vertebral bodies 7, 9. It has a height such that it allows, when it is positioned, the anatomical height of the disc 4 to be restored and the anterior common ligament 6 to be reset at anatomical tension.

In practice, an ablation of the inter-spinous ligament complex is carried out via the lateral access route, then the vertebrae 2, 3 are separated and the posterior implant 10 is positioned between the spinous processes 17, directly behind the surfaces 8, that is to say, at the lamina/spinous process junction. The flexibility of the lugs 16 does not inhibit this insertion. The two lugs 16 which are located at the side at which the implant 10 is inserted can be secured in a position turned towards each other in order to facilitate the insertion of the implant 10.

Each cord 21 is then engaged through the ring which it comprises and is secured tightly around the corresponding process 17 by sliding through this ring. The ring is then crimped to the cord 21 in order to keep the cord in a position for securing the process 17.

The implant 10, being secured in this manner, can be stressed in terms of both compression and extension.

The implant 11 is itself inserted between the vertebral plates of the two vertebrae 2, 3 via the same posterior/lateral access route as that used during a dissectomy. As shown by FIG. 4, the positioning of this implant 11 is carried out by means of an instrument 25 which comprises an introduction tube 26 which is provided with a piston 27 and a piston rod 28. The implant 11 is engaged, with compression, in this introduction tube and is expelled therefrom at the moment when it is positioned, by means of the piston 27.

The implants 10 and 11 jointly allow the anatomical spacing of the vertebrae 2, 3 to be re-established both between the surfaces 8 and between the vertebral plates, but also, and above all, the anterior common ligament 6 and the supra-spinous posterior ligament 5 to be conserved, with these ligaments being placed at anatomical tension.

When the vertebral column flexes forwards, the supra-spinous posterior ligament 5 can then once more ensure the anatomical function thereof of limiting the movement. The implant 10 allows, owing to its ability to be extended, the action of this ligament to be assisted and controlled. Simultaneously, the implant 11 restores the shock-absorbent function of the disc 4 and takes up the stresses applied in terms of pressure by the superior vertebral body 7 on the inferior vertebral body 9, with relief being provided for the peripheral annulus fibrosis. In this manner, it provides progressive absorption of shocks for this superior vertebral body 7, with any risk of contact between the vertebral bodies 7, 9 being prevented.

When the vertebral column flexes backwards, the anterior vertebral ligament 6 can again ensure the anatomical function thereof of progressively limiting the movement. Simultaneously, the implant 10 is compressed and then assists the surfaces 8 in the function thereof as hinges and of posterior balancing.

FIGS. 7 and 8 show that the inter-corporeal implant 11 can also, instead of or in addition to an inter-corporeal implant 11 as illustrated in FIGS. 1 to 6, be provided to replace and/or assist the nucleus. As shown in FIG. 7, it can then have a general "bean" or "omega"-like shape, with a central portion which is extended by two lateral lobes protruding at the posterior side or, as shown in FIG. 8, be in the form of a sphere which is provided with an equatorial lip which reduces the risk of displacement thereof. In the second case, the implant 11 comprises the sphere 11a and a ring 11b which forms the lip, the opening of this ring 11b having a diameter less than that of the sphere 11a and the sphere 11a being engaged with deformation through this opening, then being fixed to the ring 11b.

FIG. 9 shows that the posterior implant 10 can have an "H"-like shape and comprise a clip 30 which secures two lateral lugs 10a of this implant in a deformed state, in which the lugs 10a are brought closer towards each other. The clip 30 thereby allows easier lateral insertion of the implant 10 between the spinous processes 17 of the vertebrae 2, 3 being treated, until the non-deformed lugs are brought against the processes 17, and the clip 30 is then withdrawn in order to deploy the lugs 10a and, in this manner, secure the implant in position.

It will be appreciated from the above that the invention provides a decisive improvement over the prior art, by providing an assembly which allows completely functional stabilization of vertebrae which sustain both disc degeneration and ligament distension, as well as possibly wear of the surfaces, whilst being relatively simple to implant and relatively non-invasive. In this manner, this assembly forms a relief prosthesis having a dual effect.

It will be appreciated that the invention is not limited to the embodiment described above by way of example, but instead that it comprises all of the variants thereof which fall within the scope of protection defined by the appended claims.

What is claimed is:

1. A system for stabilizing a pair of adjacent vertebrae, comprising:
    a posterior implant for positioning between an upper spinous process and a lower spinous process of the adjacent vertebrae, the posterior implant comprising:
       a inter-spinous portion having an upper surface for engagement with the upper spinous process and a lower surface for engagement with the lower spinous process, the inter-spinous portion having a thickness between the upper surface and the lower surface sufficient to restore anatomical tension to a supra-spinous posterior ligament extending between the upper and lower spinous processes,
       an upper pair of lugs extending from the inter-spinous portion for interfacing with the upper spinous process, and
       a lower pair of lugs extending from the inter-spinous portion in a direction substantially opposite from the upper pair of lugs, the lower pair of lugs for interfacing with the lower spinous process,
       wherein at least one of the upper lugs and at least one of the lower lugs is movable between an insertion configuration and an implantation configuration, where the insertion configuration for the at least one of the upper and lower lugs is substantially perpendicular to the implantation configuration;
    wherein the posterior implant comprises a flexible, resilient material to allow motion between the adjacent vertebrae and to allow the at least one of the upper and lower lugs to resiliently return to the implantation configuration from the implantation configuration;
    a removable clip for engagement with the at least one of the upper and lower lugs to selectively maintain the at least one of the upper and lower lugs in the insertion configuration; and
    an anterior implant for positioning within a disc space between the adjacent vertebrae, the anterior implant having a thickness between an upper surface and a lower surface to restore anatomical tension to an anterior vertebral ligament extending between the pair of adjacent vertebrae.

2. The system of claim 1, wherein the anterior implant comprises the flexible, resilient material to allow motion between the adjacent vertebrae.

3. The system of claim 2, wherein the posterior implant and the anterior implant comprise a casing surrounding the flexible, resilient material.

4. The system of claim 1, wherein the anterior implant comprises a spherical portion deformably engaged with a ring portion.

5. The system of claim 4, wherein the spherical portion has a spherical diameter in a non-deformed configuration that is greater than a diameter of an inner opening defined by the ring portion.

6. The system of claim 5, wherein the ring portion is positioned adjacent an equator of the sphere.

7. The system of claim 1, wherein the anterior implant is elongated and curved along its length between a first end portion and a second end portion in an implantation configuration.

8. The system of claim 7, wherein the anterior implant is resiliently deformable between the implantation configuration and an insertion configuration, wherein the anterior implant is substantially straight along its length between the first end portion and the second end portion in the insertion configuration.

9. The system of claim 8, further comprising instrumentation for inserting the anterior implant, the instrumentation comprising:
    an elongated tube having a passageway extending there through from a proximal portion to a distal portion, the passageway sized to receive the anterior implant in its insertion configuration adjacent the proximal portion of the tube and to allow the anterior implant to be passed through the passageway and out of the tube into the disc space adjacent the distal portion of the tube; and
    a rod component for urging the anterior implant through the passageway, at least a portion of the rod component sized to extend within the passageway.

10. The system of claim 1, wherein the posterior implant and the anterior implant are sized and shaped for insertion via a common access route.

11. The system of claim 10, wherein the common access route comprises a posterior approach.

12. The system of claim 10, wherein the common access route comprises a lateral approach.

13. A spinal implant system for positioning between an upper vertebra and a lower vertebra, the system comprising:
    a posterior implant for positioning between a spinous process of the upper vertebra and a spinous process of the lower vertebra, the posterior implant comprising:
       a central portion having an upper surface for engagement with the spinous process of the upper vertebra and a lower surface for engagement with the spinous process of the lower vertebra, the inter-spinous portion having a thickness between the upper surface and the lower surface sufficient to restore anatomical tension to a supra-spinous posterior ligament extending between the upper and lower spinous processes,
       an upper pair of projections extending from the central portion for interfacing with the spinous process of the upper vertebra, and
       a lower pair of projections extending from the central portion in a direction substantially opposite from the upper pair of projections, the lower pair of projections for interfacing with the spinous process of the lower vertebra,
       wherein at least one of the upper projections and at least one of the lower projections is resiliently movable between an insertion configuration and an implantation configuration, the insertion configuration for the at least one of the upper and lower projections being substantially perpendicular to the implantation configuration;
    wherein the posterior implant comprises a flexible, resilient material surrounded by a woven casing to allow motion between the spinous process of the upper vertebra and the spinous process of the lower vertebra;
    a clip engaged with the at least one of the upper and lower projections to maintain the at least one of the upper and lower projections in the insertion configuration, the clip removable to allow the at least one of the upper and lower projections to resiliently move to the implantation configuration; and
    an anterior implant for positioning within a disc space between a vertebral body of the upper vertebra and a vertebral body of the lower vertebra, the anterior implant having a thickness between an upper surface and a lower surface to restore anatomical tension to an anterior vertebral ligament extending between the pair of adjacent vertebrae, wherein the anterior implant comprises a flexible, resilient material surrounded by a woven casing to allow motion between the vertebral body of the upper vertebra and the vertebral body of the lower vertebra;

wherein the posterior implant and the anterior implant are sized and shaped for insertion via a common access route.

14. The system of claim 13, wherein the common access route comprises a posterior approach.

15. The system of claim 14, wherein the posterior implant further comprises an upper channel and a lower channel, the upper and lower channels for receiving elongated fixation devices for securing the posterior implant to the spinous processes of the upper and lower vertebrae.

16. The system of claim 13, wherein the anterior implant comprises a spherical portion deformably engaged with a ring portion, the ring portion for limiting movement of the anterior implant.

17. The system of claim 16, wherein the spherical portion has a spherical diameter in a non-deformed configuration that is greater than a diameter of an inner opening defined by the ring portion.

18. The system of claim 17, wherein the spherical portion is deformed due to engagement with the ring portion adjacent an equator of the sphere.

19. The system of claim 13, wherein the anterior implant is resiliently deformable between the insertion configuration and the implantation configuration, the anterior implant being elongated and curved along its length in the implantation configuration, and substantially straight along its length in the insertion configuration.

20. The system of claim 19, further comprising instrumentation for inserting the anterior implant, the instrumentation comprising:

an elongated tube having a passageway extending from a proximal opening to a distal opening, the passageway sized to receive the anterior implant in its insertion configuration from the proximal opening of the tube and to allow the anterior implant to be passed through the passageway and out of the distal opening of the tube into the disc space; and a rod component for urging the anterior implant through the passageway, at least a portion of the rod component sized to extend within the passageway.

* * * * *